United States Patent [19]

Hoenig

[11] Patent Number: 4,527,558
[45] Date of Patent: Jul. 9, 1985

[54] SCAVENGER SYSTEM

[75] Inventor: Richard Hoenig, East Aurora, N.Y.
[73] Assignee: The BOC Group, Inc., Montvale, N.J.
[21] Appl. No.: 507,396
[22] Filed: Jun. 24, 1983
[51] Int. Cl.³ .......................................... A61M 16/00
[52] U.S. Cl. ............................ 128/205.24; 128/204.26; 128/205.19; 128/910
[58] Field of Search .............. 128/910, 205.12, 201.27, 128/201.28, 205.19, 203.28, 205.17, 204.18, 205.24, 204.26; 137/887; 138/30

[56] References Cited

U.S. PATENT DOCUMENTS

| | | | |
|---|---|---|---|
| 3,721,239 | 3/1973 | Myers | 128/205.12 |
| 4,188,946 | 2/1980 | Watson et al. | 128/910 |
| 4,265,239 | 5/1981 | Fischer, Jr. et al. | 128/910 |
| 4,291,689 | 9/1981 | Hay | 128/910 |
| 4,312,339 | 1/1982 | Thompson, Sr. | 128/910 |

Primary Examiner—Henry J. Recla
Attorney, Agent, or Firm—Roger M. Rathbun; Larry R. Cassett

[57] ABSTRACT

A gas scavenger system is disclosed for use particularly with anesthetic administering equipment utilizing a demand valve for providing anesthetic gas to the patient. The gas scavenger system includes a collection manifold that collects the waste gases as they leave the normal exhaust ports of the demand valve. A flexible tubing means then carries those collected gases to a surge chamber prior to eventual discharge into a vacuum system. The surge chamber provides an interface between the vacuum system and the collection manifold and is connected to the vacuum system through a predetermined sized orifice which limits the flow to the vacuum system to a maximum known flow. The surge chamber normally allows continuous flow through the orifice to the vacuum system but is sized to accumulate an excess of flow from the collection manifold under abnormal conditions such as is occasioned when a patient coughs to allow time to remove the gases through the orifice and thus to prevent leakage to atmosphere. The surge chamber itself is directly connected to ambient through a known, fixed resistance of hydrophobic material such that an excess in pressure in the surge chamber above a maximum amount that determined by the known, fixed resistance is bled to atmosphere. Thus, in the event of an occlusion in the vacuum line, the patient is always assured a path for exhalation. Also, in the event the vacuum system draws gas at a faster flow rate than that of waste gases entering the surge chamber from the collection manifold, gas will be drawn from the ambient through the known, fixed resistance.

7 Claims, 3 Drawing Figures

SCAVENGER SYSTEM

BACKGROUND OF THE INVENTION

This invention relates to scavenger systems utilized to remove waste gases including anesthetic gases from areas where such gases are susceptible of inhalation by personnel.

There are, of course, many different types of machines adapted to provide an anesthetic gas to a patient and various different anesthetic agents are available for that purpose, both in liquid form to be vaporized for addition to a gas, as well as gaseous forms such as nitrous oxide.

One difficulty that the use of such agents has in common, however, is the need for removal of waste gases exhaled by the patient or that may otherwise enter the local environment during an over-pressure condition through exhalation valves. It is believed that such waste gases, containing the anesthetic agent, are unhealthy for continuous breathing by personnel, such as doctors, nurses, etc., that of necessity must work for long periods of time in that environment.

Thus, there have been numerous means and devices used to scavenge or prevent those waste gases from entering the local environment. One means readily available for such removal is the normal central vacuum system available in hospitals, which operate at a vacuum level of about $-15$ to $-19$ inches of mercury vacuum.

Typically, the waste anesthetic gases are discharged into the local environment through a biased valve such as a pop-off valve, or through exhaust ports found in typical demand valves. In the use of such demand valves the patient's attempt to inhale draws a slight vacuum that opens a main valve through which the anesthetic gas passes to the patient and the patient exhales through a check valve mechanism in the demand valve; the waste exhalation gases, thus passing directly to the environment through the exhaust ports. Normally, such demand valves provide a mixture of oxygen and nitrous oxide to the patient.

The solutions heretofore proposed and used have, in some manner, captured those waste gases immediately upon their passing through some type of exhaust valve and then channeling the same to the hospital vacuum system. Problems arise in interfacing between the check valve or exhaust valve that basically sees and operates by the pressures associated with the patient circuit and the vacuum systems in the hospitals. Although there must be fluid communication there-between, the vacuum system, if allowed to act upon such exhaust valves can prevent the normal valve operation. Also, there is need for means to allow the reservoir to account for the difference in flows between the patient's exhalation which is cyclical and the steady flow to the vacuum system.

Obviously, directly connecting the vacuum system to the check or exhaust valve would supply sufficient vacuum to open that valve continuously, thus the interface is needed to prevent the line vacuum from affecting the normal valve operation. Also, as to flow, the patient delivers an intermittent flow of gases during exhalation while, during inhalation, there is no flow from the patient. The exhalation flow for a normal resting patient may be in the order of 8-12 liters/minute. The vacuum supply, on the other hand is a constant draw and thus, a reservoir is used to contain the higher flows of exhaled gases until the vacuum system can catch up and remove those gases.

Presently, interfacing reservoirs are of a closed system where the reservoir is a closed container and has positive and negative valves. A positive check valve operates at normally about 10 cm $H_2O$ and allows a path for the patient to exhale in the event the vacuum line is occluded or the vacuum system discontinued. A negative check valve is also present and is normally set to about $\frac{1}{2}$ cm $H_2O$ and prevents full vacuum from ever reaching the patient.

By the use of these valves in the closed system, the patient is protected. The valves, themselves, however, add a further source of trouble. At the extremely low pressure and vacuum points, such valves are quite difficult to calibrate and, of course, the valves are always subject to malfunction due to sticking.

Open systems can also be used to interface between the exhaust valve and the vacuum supply where the reservoir itself is completely open to the surrounding ambient, however, some resistance between the reservoir and that ambient is desirable to prevent all of the waste gases from entering the ambient atmosphere.

SUMMARY OF THE INVENTION

The present invention overcomes the aforesaid difficulties in providing a scavenging system for use with a central vacuum system by providing a reservoir surge chamber of sufficient volume to receive and contain the higher than normal patient exhalations. The exhalation gases are obtained by surrounding the exhalation valve with a collection manifold that traps the anesthetic laden gases before they can be released to the environment. The surge chamber is also connected to a source of vacuum, such as a hospital system, through an orifice that allows a maximum predetermined flow of gas from the surge chamber to the vacuum system. A known, fixed resistance is provided between the interior of the surge chamber and the ambient surroundings and which is used to relieve pressure to the ambient at too high levels as well as draw ambient air into the chamber at excessive vacuum levels. The known, fixed resistance is formed by a tubing containing a resistive material through which the gas may travel. The preferable material is a polyurethane foam due to its fairly uniform resistance to flow and its hydrophobic properties.

In normal use, the exhaled gases collected by the collection manifold pass fairly directly through the surge chamber in a preferential flow path with little resistance and thence through a flow restriction to the vacuum system.

In the event of an abnormality, i.e. an unusually high pressure or high vacuum, flow will pass, respectively, to ambient through the known, fixed resistance or from ambient through the known, fixed resistance. By therefore selecting the resistance to be a desired valve, the collection manifold is protected from unusually adverse conditions either by high pressure or high vacuum. In the event of a higher than normal flow from the patient, i.e. a cough, the surge chamber has sufficient volume to accept the surge until the normal vacuum can catch up and remove that gas.

The surge chamber further has a valving means at its lower-most point, to allow the automatic removal of condensation as it builds up, thus protecting the system from plugging of any flow paths by an accumulation of water.

BRIEF DESCRIPTION OF THE DRAWINGS

The invention is diagrammatically illustrated by way of example in the drawings appended hereto, in which.

DESCRIPTION OF PREFERRED EMBODIMENT

Figure 1:
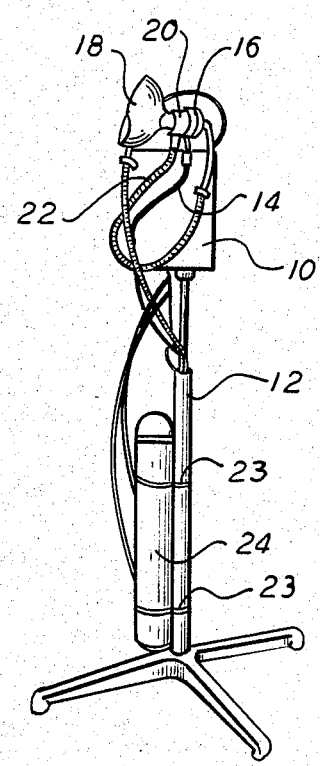
FIG. 1 is a perspective view of a commercial machine used to anesthetize patients and including the present scavenging system.

In FIG. 1, there is shown an apparatus for administering nitrous oxide in mixture with oxygen to a patient and incorporating therein a scavenger system constructed in accordance with the present invention. As further described, the invention will be illustrated as used on an anesthesia machine utilizing a demand valve for administering an anesthetic to a patient, however, it will be understood that this invention is adaptable to other valves that emit waste anesthetic gases, such as check or pop-off valves.

In the illustrated version, however, a mixing head 10 is mounted on a stand 12 for convenience and ease of use. The head 10 essentially comprises known means of mixing oxygen and nitrous oxide in proportions selected by the user. The supply of oxygen and nitrous oxide may be provided by containers mounted to the stand 12 or by pipeline supply available in hospitals.

The mixed nitrous oxide/oxygen is thus supplied by suitable tubing 14 to a demand valve 16 for administration to a patient by means of a facemask 18. The overall unit is commercially available, one of which being sold by Fraser Harlake Inc. under its trademark "Nitronox."

The scavenger system of the present invention is adapted to be useable with that or other commercial machines, and includes a collection manifold 20 that surrounds the exhaust ports of the demand valve 16 as will be later explained. Waste anesthetic gases received by the collection manifold 20 pass through tubing 22 to the surge chamber 24 which, for convenience, can be mounted to the stand 12 by means such as clamps 23.

Figure 2:
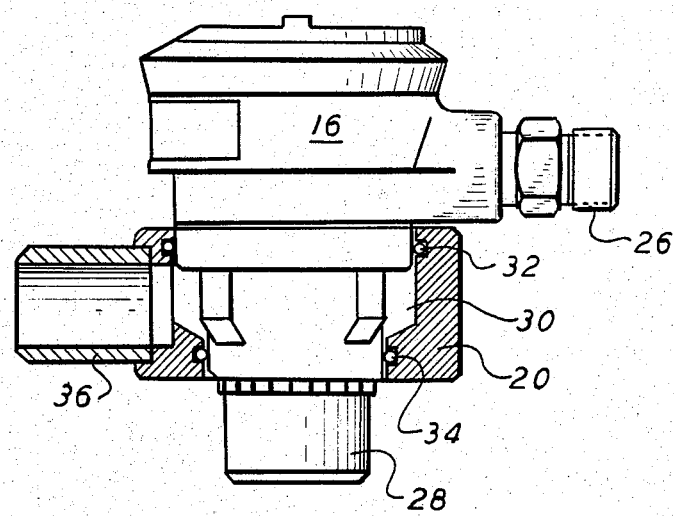
FIG. 2 is a perspective view, partly in cross section, of a collection manifold fitted to a demand valve.

Turning now to FIG. 2, there is shown the demand valve 16 with the collection manifold 20 mounted in place. The demand valve 16 is a readily available item having an inlet 26 that receives the nitrous oxide-oxygen mixture from tubing 14 (FIG. 1) and an outlet 28 that fits into the mask 18 (FIG. 1) for administering the gas to a patient. The collection manifold 20 surrounds the exhaust valve of demand valve 16 and collects the waste gases exhaled by the patient within annular chamber 30. The annular chamber 30 is sealed from the surrounding environment by means such as O-rings 32 and 34 forming a tight seal against the outer surface of the demand valve 16.

Thus, all gases exhaled by the patient pass into the annular chamber 30 and are prevented from entering the surrounding environment. The collection manifold 20 has an outlet means, such as tapered fitting 36 for connection to tubing 22. In the preferred embodiment, the inlet 26 of the demand valve 16 is threaded and the tapered fitting 36 are of significantly differing diameters so as to prevent inadvertent confusing between the tubings 14 and 22 causing incorrect connections.

Figure 3:
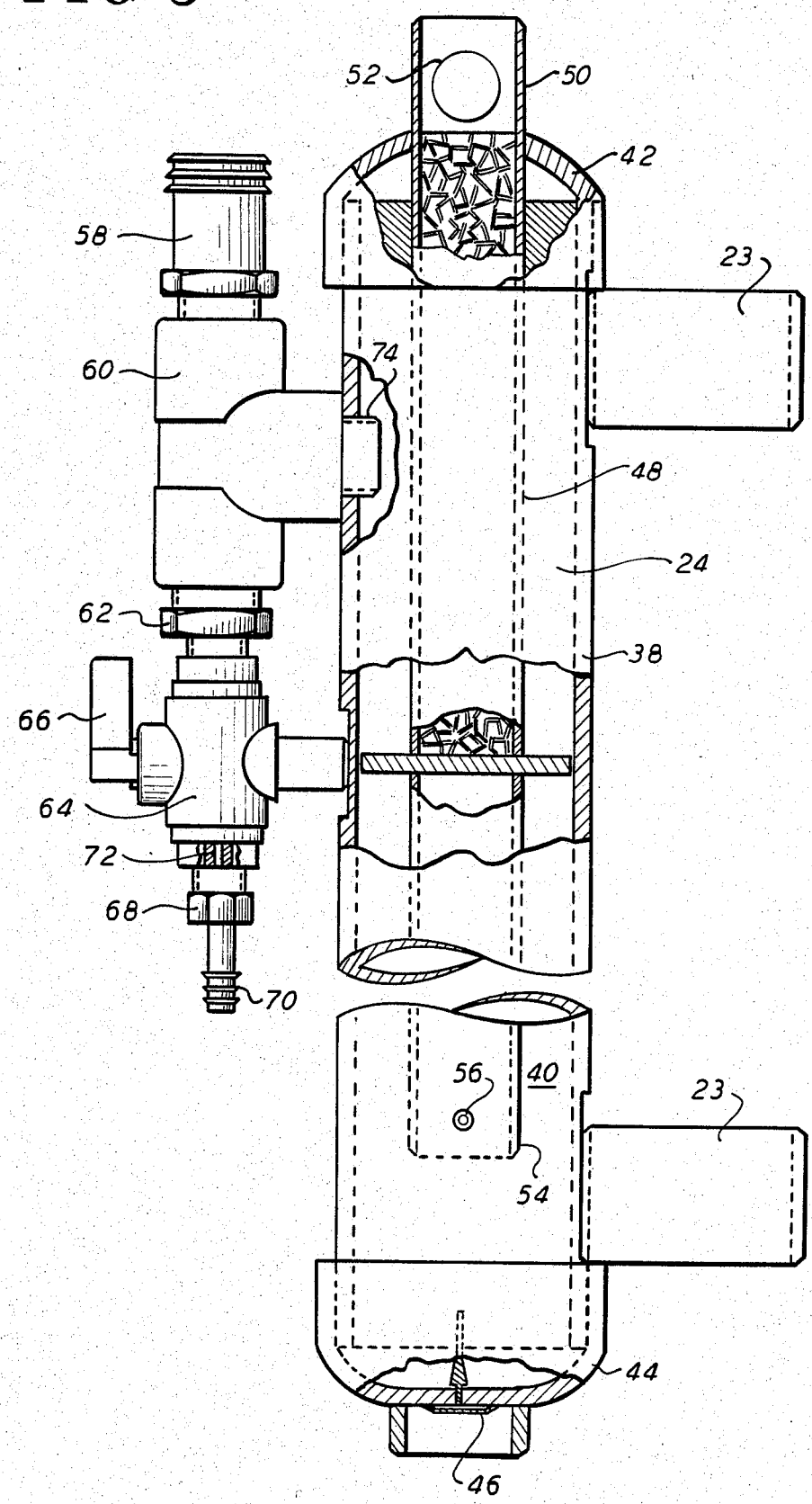
FIG. 3 is a perspective view, partly in cross section, of the surge chamber used in the present invention.

Turning now to FIG. 3, there is shown a side view, partly in section, of the surge chamber 24 used as a part of this invention. The surge chamber 24 comprises an outer cylindrically shaped housing 38 enclosing therein a closed chamber 40. The housing 38 has a top cap 42 which covers an end of housing 38. Typically, the top cap 42 is sealed to the housing 38 by an adhesive weld in a gas-tight relationship.

A bottom cap 44 is sealed to the other end of the housing 38 in similar fashion. A flexible rubber valve 46 is located in the bottom cap 44 and flexes away from its seat upon the accumulation of amounts of moisture built up by condensation in the bottom of the housing 38. Typically, such flexible rubber valve 46 opens upon the accumulation of about one inch of water. After the excess water is drained, the flexible rubber valve 46 resumes its normally closed position.

A fixed resistance of known valve is provided and forms a flow path between the closed chamber 40 within surge chamber 24 and the ambient air. As shown, the fixed resistance comprises a cylindrical tube 48 depending from the top cap 42 downwardly within the closed chamber 40.

The upper end 50 of the cylindrical tube 48 extends through top cap 42 and is sealed thereto around its inner periphery by an adhesive bonding. Upper end 50 is open to the ambient atmosphere at its top and also through a plurality of apertures 52 that are formed therein. As will be seen, the use of a plurality of apertures 52, the complete occlusion of the upper end 50 of cylindrical tube 48 is rendered extremely difficult.

The lower end 54 of cylindrical tube 48 depending within the closed chamber 40 is also open. The cylindrical tube 48 is held in position within the surge chamber 24 by a support means such as a pin 56 that is fitted through the housing 38 and is of sufficient length as to have its ends abut the inside surface of cylindrical tube 48. The interior of the cylindrical tube 48 is filled with a resistive material to create a known, fixed resistance that is roughly proportional to the length of cylindrical tube 48. A preferred material useable is polyurethane foam due to its fairly uniform resistance and its hydrophobic properties.

A preferential flow path is provided to normally convey gas from the patient to a suitable source of vacuum, typically, that source is a central vacuum system found in hospitals and having available vacuum of about −15 to −19 in. Hg.

As shown, the preferential flow path comprises a threaded connection 58 which is connected (not shown) to tubing 22 (FIG. 1) and which conveys gas from the collection manifold 20.

Continuing on with the preferential flow path, the threaded connector 58 is joined to a tee 60 having a straight through path connecting to an adapter 62 and thus into a ball valve 64.

Ball valve 64 is essentially standard, having off-on positions operable by handle 66, however, in its normally off position, the ball valve 64 is modified slightly in that an orifice is provided in the internal ball such that flow can pass through ball valve 64 even in its off position. In the preferred form, for normal vacuum sources, the orifice is a drilled hole of approximately 1/32" diameter and which allows a flow through ball valve 64 of approximately 8–12 liters per minute, the purpose of which will be later explained.

The flow of gas leaving ball valve 64 passes through a fitting 68 having a tapered end 70 to receive a flexible tubing (not shown) for connection to the hospital vacuum system. A further orifice 72 is provided in the fitting 68 and is sized to allow a flow there-through of about 36–40 liters per minute. Thus, as may be seen, by turning handle 66 of ball valve 64, the maximum flow through the preferential flow path i.e. from the patient to the vacuum system can be adjusted from 8–12 liters per minute to 36–40 liters per minute.

A further path for the flow of gas from the patient is through the 90° outlet 74 that is fitted into and in a gas-tight seal with housing 38 and thus enter closed chamber 40. The operation of the scavenger system can now be outlined in more detail. When the patient exhales, the exhalation waste gases containing harmful agents pass through the demand valve 16 and are collected in collection chamber 20 before those gases can enter the surrounding environment. The waste gases are then normally carried to the hospital vacuum system through the preferred flow path. During normal exhalation, the flow of waste gases from a patient may be in the order of 8–12 liters/minute and, assuming the ball valve 64 is in the open position, the waste gases are easily carried to the vacuum since flow is limited only by orifice 72 at 36 to 40 liters/minute. Under normal conditions, therefore, outside air is continuously drawn into closed chamber 40 through the fixed resistance. Even when the ball valve 64 is in the closed position, 8–12 liters of flow can pass there-through and thus, the vacuum system can normally keep up to the flow of gases from the patient. The ball valve 64 can be therefore moved from open to closed position to reduce the maximum flow to the hospital vacuum system. This is advantageous in the event the vacuum system is being overloaded and it is necessary to limit the flow from certain equipment to protect the level of vacuum in the central system.

In the event of an unusually large surge or flow from the collection chamber 20, such as if the patient was to cough, the closed chamber 40 can temporarily take up that surge until the vacuum system can catch up. The patient does not encounter uncomfortable resistance due to the fixed resistance that allows the closed chamber 40 to vent to atmosphere above a predetermined pressure set by the fixed resistance. Even if, due to a malfunction, the vacuum system is shut down or a vacuum line occluded, the patient can exhale through the fixed resistance to atmosphere.

In the converse, the fixed resistance path between the closed chamber 40 and the ambient operates to prevent an unusually high vacuum from ever reaching the collection chamber 20 to affect the normal operation of the demand valve 16. In the event of such an unusually high vacuum, the ambient air can enter the closed chamber 40 through the fixed resistance and therefore provide an effective limit on the amount of vacuum in the closed chamber 40, thus also in collection chamber 20.

Thus, the fixed resistance between closed chamber 40 and atmosphere provided over pressure and over vacuum protection without moving valves, yet the resistance can very accurately determined those safety conditions and be manufactured easily and repeatedly.

As a further safety feature, the flexible rubber valve 46 located in the lower-most point of the surge chamber 24 opens automatically upon the accumulation of any significant amount of water in the surge chamber 24 and thus dumps the water out of the system. The open lower end 54 of cylindrical tube 48 is thereby protected from occlusion by a build-up of water.

I claim:

1. A gas scavenger system for conveying waste exhalation gas to a vacuum system from an anesthetic apparatus having a demand valve for administering an anesthetic gas to a patient and having exhaust ports for normally passing the waste exhalation gas from the patient to atmosphere, said gas scavenger system comprising collection manifold means receiving the waste exhalation gas from the exhaust ports, surge chamber means connected to said collection manifold means and adapted to receive the waste exhalation gas therefrom, said surge chamber means having an outlet connectable to the vacuum system and having a valve means limiting the flow of gas from said surge chamber means to the vacuum system, said surge chamber means containing a predetermined volume to receive normal excess flows occasioned by exhalation from the patient, fixed resistance means forming a flow path between said surge chamber means and the surrounding atmosphere, said fixed resistance means comprising an elongated tube extending essentially within the interior of said surge chamber means, said tube having one end thereof open within said surge chamber means and having the other end open to surrounding atmosphere external of said surge chamber means, said tube containing a substantially hydrophobic substance having a known flow resistance and which allows the flow of gas through said tube to the atmosphere when the pressure in said surge chamber means exceeds a predetermined maximum value and allows the flow of gas through said tube to said surge chamber means from the atmosphere when the vacuum in said surge chamber means exceeds a predetermined value.

2. A gas scavenger system as in claim 1, wherein said substance is polyurethane foam.

3. A gas scavenger system as in claim 1, wherein said surge chamber means further has a relief valve in its lower portion to relieve build up of liquid in said surge chamber means when said liquid reaches a predetermined head.

4. A gas scavenger system as in claim 1 wherein said valve means is a multi-position valve adapted to vary the maximum flow of gas from said surge chamber means.

5. An interface surge chamber for receiving gas of a varying flow to direct that gas to a constant vacuum source, said interface surge chamber comprising an inlet for receiving gas from said varying flow source and an outlet connectable to the vacuum system, a valve means limiting the flow of gas from said interface surge chamber to the vacuum system, said interface surge chamber having a predetermined volume to receive and contain excess flows from the varying flow source, fixed resistance means forming a flow path between said interface surge chamber and the surrounding atmosphere, said fixed resistance comprising an elongated tube extending essentially within the interior of said interface surge chamber, said tube having one end thereof open to atmosphere through said interface surge chamber and the other end within said interface surge chamber, said tube containing a substantially hydrophobic substance of predetermined flow resistance to allow the flow of gas through said tube to the atmosphere when the pressure in said interface surge chamber exceeds a predetermined value and allows flow of gas through said tube to said surge chamber from the atmosphere when the vacuum in said surge chamber exceeds a predetermined value.

6. An interface surge chamber as in claim 1, wherein said substance is polyurethane foam.

7. Gas scavenger system as in claim 1, wherein said interface surge chamber further has a relief valve in its lower portion to relieve build up of liquid in said interface surge chamber when said liquid reaches a predetermined head.

* * * * *

UNITED STATES PATENT AND TRADEMARK OFFICE
CERTIFICATE OF CORRECTION

PATENT NO. : 4,527,558
DATED : July 9, 1985
INVENTOR(S) : Richard Hoenig

It is certified that error appears in the above-identified patent and that said Letters Patent are hereby corrected as shown below:

Col. 5, line 53, "provided" should read
-- provides --.

Col. 6, line 2, "receiving" should read
-- adapted to receive --;

line 5, delete "adapted to receive";

line 61, "claim 1" should read
-- claim 5 --.

Signed and Sealed this

Twenty-eighth Day of January 1986

[SEAL]

Attest:

DONALD J. QUIGG

Attesting Officer

Commissioner of Patents and Trademarks